(12) United States Patent
Gao et al.

(10) Patent No.: US 7,576,205 B2
(45) Date of Patent: Aug. 18, 2009

(54) DETECTABLE THREADING INTERCALATOR

(75) Inventors: Zhiqiang Gao, Singapore (SG); Hong Xie, Singapore (SG); Fang Xie, Sydney (AU)

(73) Assignee: Agency for Science, Technology & Research, Singapore (SG)

( * ) Notice: Subject to any disclaimer, the term of this patent is extended or adjusted under 35 U.S.C. 154(b) by 483 days.

(21) Appl. No.: 11/152,495

(22) Filed: Jun. 13, 2005

(65) Prior Publication Data

US 2006/0281922 A1  Dec. 14, 2006

(51) Int. Cl.
*C07F 15/00* (2006.01)
*C12Q 1/68* (2006.01)

(52) U.S. Cl. .............. 546/10; 435/6; 546/2; 546/66
(58) Field of Classification Search ............ 546/2, 546/66, 10; 435/6
See application file for complete search history.

(56) References Cited

U.S. PATENT DOCUMENTS

| 6,399,305 B1 | 6/2002 | Makino et al. | |
| 2004/0013959 A1 | 1/2004 | Bender et al. | 430/56 |
| 2005/0004365 A1 | 1/2005 | Bender et al. | 546/70 |

FOREIGN PATENT DOCUMENTS

EP  1 065 278 A2  3/2001

OTHER PUBLICATIONS

CA Abstract No. 144:361123.
CA Abstract No. 144:138765.
CA Abstract No. 143:416889.
CA Abstract No. 141:405195.
CA Abstract No. 140:347297.
CA Abstract No. 125:47474.
CA Abstract No. 142:34147.
CA Abstract No. 140:192948.
CA Abstract No. 138:255498.
CA Abstract No. 138:106994.
CA Abstract No. 136:336733.
CA Abstract No. 140:321690.
CA Abstract No. 138:90397.
CA Abstract No. 132:194027.
CA Abstract No. 81:169931.
CA Abstract No. 81:152670.
CA Abstract No. 139:204923.
CA Abstract No. 138:39267.
CA Abstract No. 132:161722.
CA Abstract No. 127:220962.
U.S. Appl. No. 10/866,370, filed Jun. 10, 2004, Gao et al.
Shau-Fong Yen et al. "Interaction of Aromatic Imides with Deoxyribonucleic Acid. Spectrophotometric and Viscometric Studies". *Biochemistry* (1982), 21, 2070-2076.

Natalia C. Tansil et al. "Direct Detection of DNA with an Electrocatalytic Threading Intercalator". *Anal. Chem.*, vol. 77, No. 1, (2005), 126-134.
Joseph Wang. Survey and Summary From DNA Biosensors to Gene Chips. *Nucleic Acids Research*, 2000, vol. 28, No. 16, 3011-3016.
T. Gregory Drummond et al. "Electrochemical DNA sensors". *Nature Biotechnology*, vol. 21, No. 10, (2003), 1192-1199.
Emil Paleček et al. "Electrochemistry of Nucleic Acids and Development of DNA Sensors". *Critical Reviews in Analytical Chemistry*, 32(3):261-270 (2002).
Frantisek Jelen et al. "Label-Free Determination of Picogram Quantities of DNA by Stripping Voltammetry with Sold Copper Amalgam or Mercury Electrodes in the Presence of Copper". *Anal. Chem.*, vol. 74, No. 18, (2002), 4788-4793.
Grant R. Sutherland et al. "The Study and Diagnosis of Human Genetic Disorders using Nucleic Acid Probes". *Nucleic Acid Probes*, Synoms, R.H. Ed.; CRC Press, Boca Raton, FL., (1989), 159-201.
Larry J. Kricka. "Nonisotopic Probing, Blotting, and Sequencing". $2^{nd}$ Ed. Academic Press Inc., San Diego, CA, (1995), 41-109.
Wujan Miao et al. "Electrogenerated Chemiluminescence. 72. Determination of Immobilized DNA and C-Reactive Protein on Au(111) Electrodes Using Tris(2,2'-bipyridyl)ruthenium(II) Labels". *Anal. Chem.* vol. 75, No. 21, (2003), 5825-5834.
Thomas J. Meyer. "Chemical Approaches to Artificial Photosynthesis". *Acc. Chem. Res.*, vol. 22, No. 5, (1989), 163-170.
Jonathan V. Caspar et al. "Photochemistry of Ru(bpy)$_3^{2+}$, Solvent Effects". *J. Am. Chem. Soc.* (1983), vol. 105, No. 17, 5583-5590.
J. Van Houten et al. "Temperature Dependence of the Photophysical and Photochemical Properties of the Tris(2,2'-bipyridyl)ruthenium(II) Ion in Aqueous Solution". *J. Am. Chem. Soc.* (1976), 98:16, 4853-4858.
Nurhan E. Tokel et al. "Electrogenerated Chemiluminescence. IX. Electrochemistry and Emission from Systems Containing Tris(2,2'-bipyridine)ruthenium(II) Dichloride[1]". *J. Am. Chem. Soc.* 94:8, (1972), 2862-2863.
Wujian Miao et al. "Electrogenerated Chemiluminescence. 80. C-Reactive Protein Determination at High Amplification with [Ru(bpy)$_3$]$^{2+}$-Containing Microspheres". *Anal. Chem.* (2004), 76, 7109-7113.
Wujian Miao et al. "Electrogenerated Chemiluminescence. 77. DNA Hybridization Detection at High Amplification with [Ru(bpy)$_3$]$^{2+}$-Containing Microspheres", *Anal. Chem.* (2004), 76, 5379-5386.
Koji Hashimoto et al. "Sequence-Specific Gene Detection with a Gold Electrode Modified with DNA Probes and an Electrochemically Active Dye". *Anal. Chem.* (1994), 66, 3830-3833.
Michael T. Carter et al. "Voltammetric Studies of the Interaction of Metal Chelates with DNA. 2. Tris-Chelated Complexes of Cobalt(III) and Iron(II) with 1,10-Phenanthroline and 2,2'-Bipyridine". *J. Am. Chem. Soc.* (1989), 111, 8901-8911.

(Continued)

*Primary Examiner*—Charanjit S Aulakh
(74) *Attorney, Agent, or Firm*—Klarquist Sparkman, LLP

(57) ABSTRACT

A threading intercalator of general formula I:

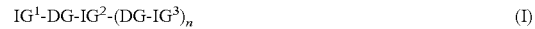

wherein $IG^1$, $IG^2$, and $IG^3$ are the same or different and represent an intercalating group comprising a planar polyaromatic group; wherein DG represents an electrochemical, a chemiluminescent, a catalytic or an electrochemiluminescent detectable group; and wherein n represents 0 or 1. This invention also relates to a process of detecting a double strand nucleic acid molecule using the threading intercalator.

17 Claims, 8 Drawing Sheets

OTHER PUBLICATIONS

Steven M. Zenman et al. "Characterization of Covalent Adriamycin-DNA Adducts". *Proc. Natl. Acad. Sci.* USA 95 (1998) 11561-11565.

Kathryn E. Erkkila et al. "Recognition and Reaction of Metallointercalators with DNA". *Chem. Rev.* (1999), 99, 2777-2795.

Andreas Rademacher et al. English Abstract of "Lösliche Perylen-Fluoreszenzfarbstoffe mit hoher Photostabilität". *Chem. Ber.* 115, 2927-2934 (1982).

Howard E. Katz et al. "Naphthalenetetracarboxylic Diimide-Based n-Channel Transistor Semiconductors: Structural Variation and Thiol-Enhanced Gold Contacts". *J. Am. Chem. Soc.* (2000), 122, 7787-7792.

Hong Xie et al. "A Nucleic Acid Biosensor for Gene Expression Analysis in Nanograms of mRNA". *Anal. Chem.* (2004), 76, 4023-4029.

Hong Xie, et al. "Amperometric Detection of Nucleic Acid at Femtomolar Levels with a Nucleic Acid/Electrochemical Activator Bilayer on Gold Electrode". *Anal. Chem.* (2004), 76, 1611-1617.

Hong Xie et al. "Highly Sensitive Amperometric Detection of Genomic DNA in Animal Tissues". *Nucleic Acids Research* (2004), vol. 32, No. 2 e15.

Adam B. Steel et al. "Electrochemical Quantitation of DNA Immobilized on Gold". *Anal. Chem.* 1998, 70, 4670-4677.

A. Juris et al. "Ru(II) Polypyridine Complexes: Photophysics, Photochemistry, Electrochemistry, and Chemiluminescence". *Coordination Chemistry Reviews*, 84 (1988) 85-277.

Dabney W. Dixon et al. "Effect of DNA Scaffolding on Intramolecular Electron Transfer Quenching of a Photoexcited Ruthenium(II) Polypyridine Naphthalene Diimide". *Inorg. Chem.* 1999, 38, 5526-5534.

Dale L. Boger et al. "A Simple, High-Resolution Method for Establishing DNA Binding Affinity and Sequence Selectivity". *J. Am. Chem. Soc.* (2001), 123, 5878-5891.

Meredith M. Murr et al. "An *Octakis*-Intercalating Molecule". *Bioorg. Med. Chem* 9 (2001), 1141-1148.

Shigeori Takenaka et al. "DNA Sensing on a DNA Probe-Modified Electrode Using Ferrocenylnaphthalene Diimide as the Electrochemically Active Ligand". *Anal. Chem.* 2000, 72, 1334-1341.

Diego A. Gianolio et al. "Tethered naphthalene diimide-based intercalators for DNA triplex stabilization", *Nucleic Acids Research*, 2000, vol. 28, No. 19.

Shigeori Takenaka et al. "Selective stabilization of a bulged duplex of d(GCGAAACGC) oligonucleotide by thymine base-substituted naphthalene diimide". *Chem. Commun.*, 1997, 115-116.

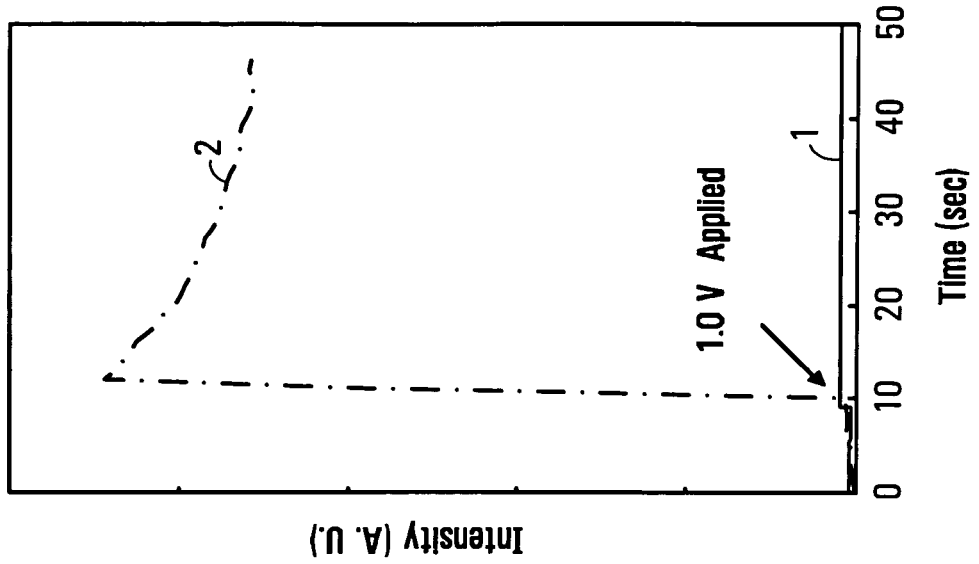
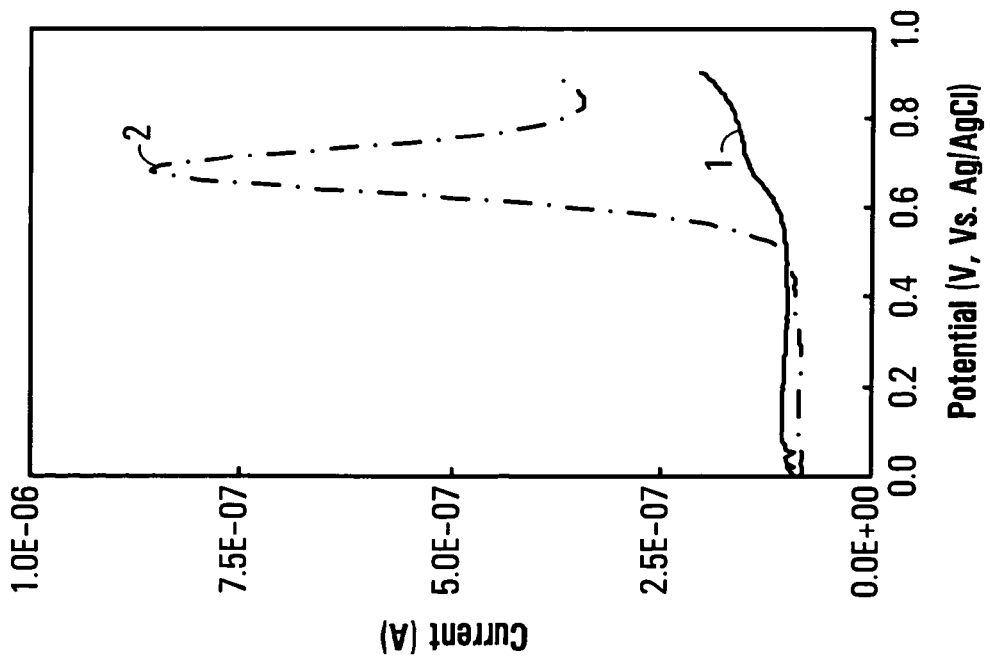
FIG. 7B
FIG. 7A

DETECTABLE THREADING INTERCALATOR

FIELD OF THE INVENTION

This invention relates to a threading intercalator, and to a process of detecting a double stranded nucleic acid molecule using the threading intercalator.

BACKGROUND OF THE INVENTION

Considerable interest has been focused on the development of ultrasensitive DNA biosensors following the completion of the Human Genome Project. These biosensors have a wide variety of potential applications that range from genotyping to molecular diagnostics. The use of fluorescently labeled oligonucleotides in conjunction with surface modification techniques affords high density DNA arrays for analyzing specific DNA sequences and gene expression, but only a few of the fluorescence-based techniques have sufficient sensitivities for the detection of DNA at sub-nanomolar levels.

Other transduction techniques, such as autoradiographic, electrochemical, chemiluminescent, and transitional metal-bipyridine complex-based electrochemiluminescentmethods (ECL) have therefore been proposed for ultrasensitive detection of DNA hybridization events. Among them, ECL has been demonstrated to be one of the most sensitive techniques. ECL is the process of generating excited states in a photoactive molecule at an electrode surface, leading to luminescence upon return to the ground state. One compound that has been extensively studied is tris(2,2'-bipyridine)ruthenium [Ru(bpy)$_3^{2+}$]. ECL of Ru(bpy)$_3^{2+}$ was reported by Tokel et al. some thirty years ago (Tokel et al., *J. Am Chem. Soc.* 1972, 94, 2862-2866). Because of its low-lying metal-to-ligand charge-transfer (MLCT) excited states, high emission quantum yields (~4.2% in H$_2$O) and long excited-state lifetimes (~600 ns), the Ru(bpy)$_3^{2+}$/tri-n-propylamine (TPA) system is usually adopted in analytical applications. ECL as a DNA detection technique has the potential to match or exceed the sensitivity of autoradiography since it enjoys the benefit of having different forms of energy for excitation and detection. The key to the ultrahigh sensitivity of ECL lies in its ultralow background noise, which is a direct consequence of having two different forms of energy for analytical signal generation and detection. Unlike fluorescence-based techniques, ECL does not involve an excitation light source and it can theoretically produce a "zero" background.

A promising approach toward the enhancement of the ECL signal is to build up multiple ECL tags on a single double stranded nucleic acid molecule (e.g. DNA). This strategy has the advantage of providing multiple redox sites, thereby greatly increasing the number of charge recombination events per target DNA molecule, and consequently enhancing the sensitivity and detection limit of a DNA biosensor. Two fundamental issues that need to be addressed in the development of multiple ECL tag systems are (i) accessibility of the ECL redox sites to the electrode and to active TPA species, and (ii) electronic independence of the redox sites to avoid intramolecular energy transfer from the excited site to a lowest-lying unoccupied molecular orbital of an acceptance site. It has been demonstrated that as little as 1.0 fM DNA is detected when Ru(bpy)$_3^{2+}$ doped polystyrene microspheres are used as ECL labels. The microspheres were shown to be beneficial both for target DNA immobilization and for amplifying ECL signal.

Threading intercalators are an important group of compounds that interact reversibly with modified or unmodified double stranded nucleic acid polymers, such as ds-DNA, ds-peptide nucleic acids, and peptide nucleic acid-nucleic acid hybrids. Some of the known threading intercalators are valuable antitumor drugs currently used for the treatment of ovarian and breast cancers. Threading intercalators share common structural features such as the presence of planar polyaromatic systems, which bind to ds-DNA by insertion between base pairs. It has also been shown that the use of an electroactive DNA intercalator as a hybridization indicator avoids labelling of the target DNA, as is commonly done in conventional DNA detection techniques, which avoids tedious labelling procedures and the use of expensive equipment. These biosensors, however, have to solve a low signal/noise ratio problem since most threading intercalators bind not only to ds-DNA but also, although to a much less extent, to single-stranded DNA (ss-DNA) molecules by electrostatic interaction. Intercalators offering better discrimination between ss- and ds-DNA are being developed for achieving greater signal/noise ratio.

BRIEF SUMMARY OF THE INVENTION

In one aspect, the present invention provides a threading intercalator of general formula I:

$$IG^1\text{-}DG\text{-}IG^2\text{-}(DG\text{-}IG^3)_n \qquad (I)$$

wherein $IG^1$, $IG^2$ and $IG^3$ are the same or different and represent an intercalating group comprising a planar polyaromatic group; DG represents a catalytic, electrochemical, a chemiluminescent, a catalytic or an electrochemiluminescent detectable group; and n and m each independently represent 0 or 1.

In another aspect, the present invention provides a process for electrochemically detecting an oligo- or poly-nucleotide sample using a threading intercalator as described herein.

In yet another aspect, the present invention provides a kit for electrochemically detecting an oligo- or poly-nucleotide sample which comprises a threading intercalator as described herein.

In one embodiment, the threading intercalator is a compound of formula VII:

(VII)

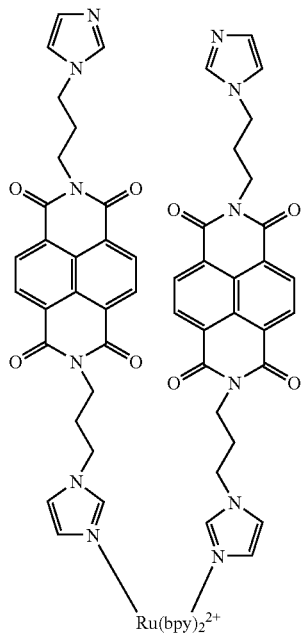

which comprises two 1,4,5,8-naphthalene diimide (ND) imidazole derivatives, which are coordinatively attached to an electrochemiluminescent Ru(bpy)$_2^{2+}$ moiety. The threading intercalator of formula VII is referred to herein as ND-Ru-ND.

In another embodiment, the threading intercalator is a compound of formula VIII:

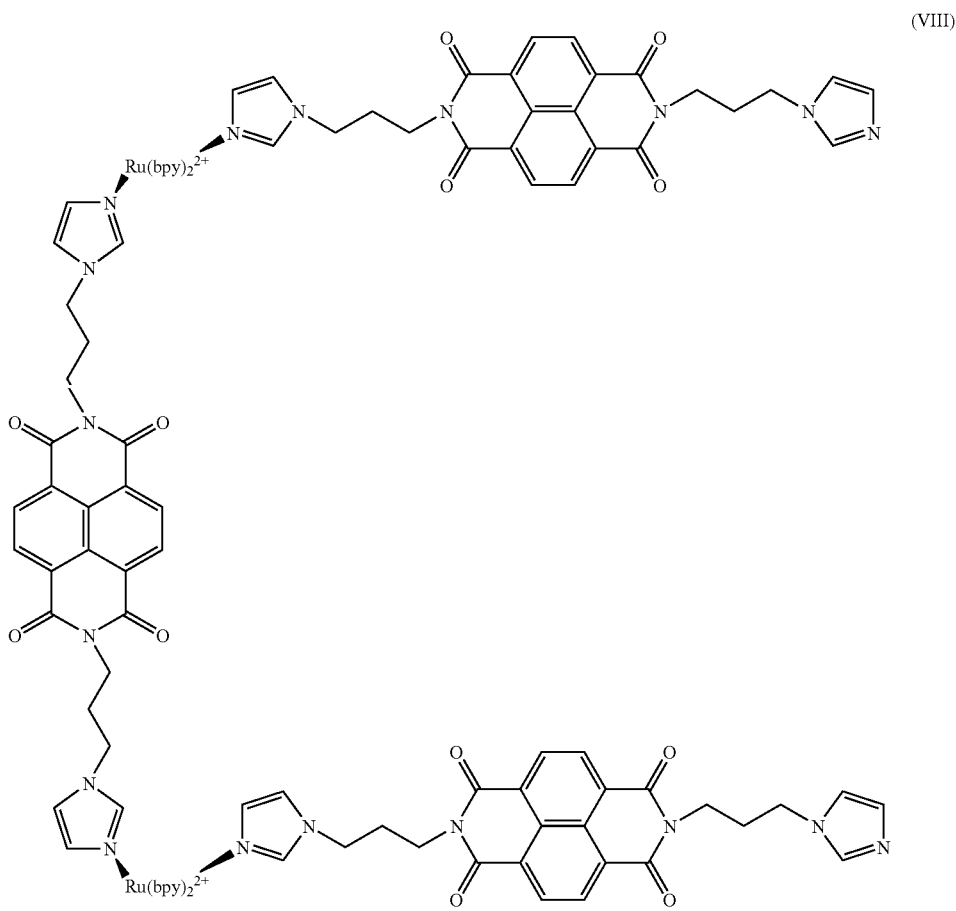

(VIII)

which comprises three 1,4,5,8-naphthalene diimide (ND) imidazole derivatives, which are coordinatively attached to two electrochemiluminescent $Ru(bpy)_2^{2+}$ moieties. The threading intercalator of formula VIII is referred to herein as ND-Ru-ND-Ru-ND.

In some embodiments, the multiple intercalating groups in the threading intercalator of formula I provides a stronger interaction between the threading intercalator and double stranded nucleic acid molecules, which in turn provides better selectivity between double stranded and single stranded nucleic acid molecules for the threading intercalator.

The above aspects of the present invention will become apparent from the following description when taken in conjunction with the accompanying figures which illustrate various embodiments of the present invention by way of example.

BRIEF DESCRIPTION OF THE DRAWINGS

Embodiments of the invention will be discussed with reference to the following Figures:

FIG. 7 shows (A) linear scan voltammograms of ND-Ru-ND bound to (1) 1.0 μM non-complementary target DNA, and to (2) 200 nM of complementary target DNA hybridized biosensors (supporting electrolyte PBS, potential scan rate 100 mV/s); and (B) ECL responses of ND-Ru-ND bound to (1) 10 nM non-complementary target DNA hybridized biosensor and (2) 100 pM complementary target DNA after ND-Ru-ND incubation (poise potential 1.0 V, pH 9.0 phosphate buffer +0.20 M TPA).

DETAILED DESCRIPTION OF THE INVENTION

Detectable Groups

Figure 1:
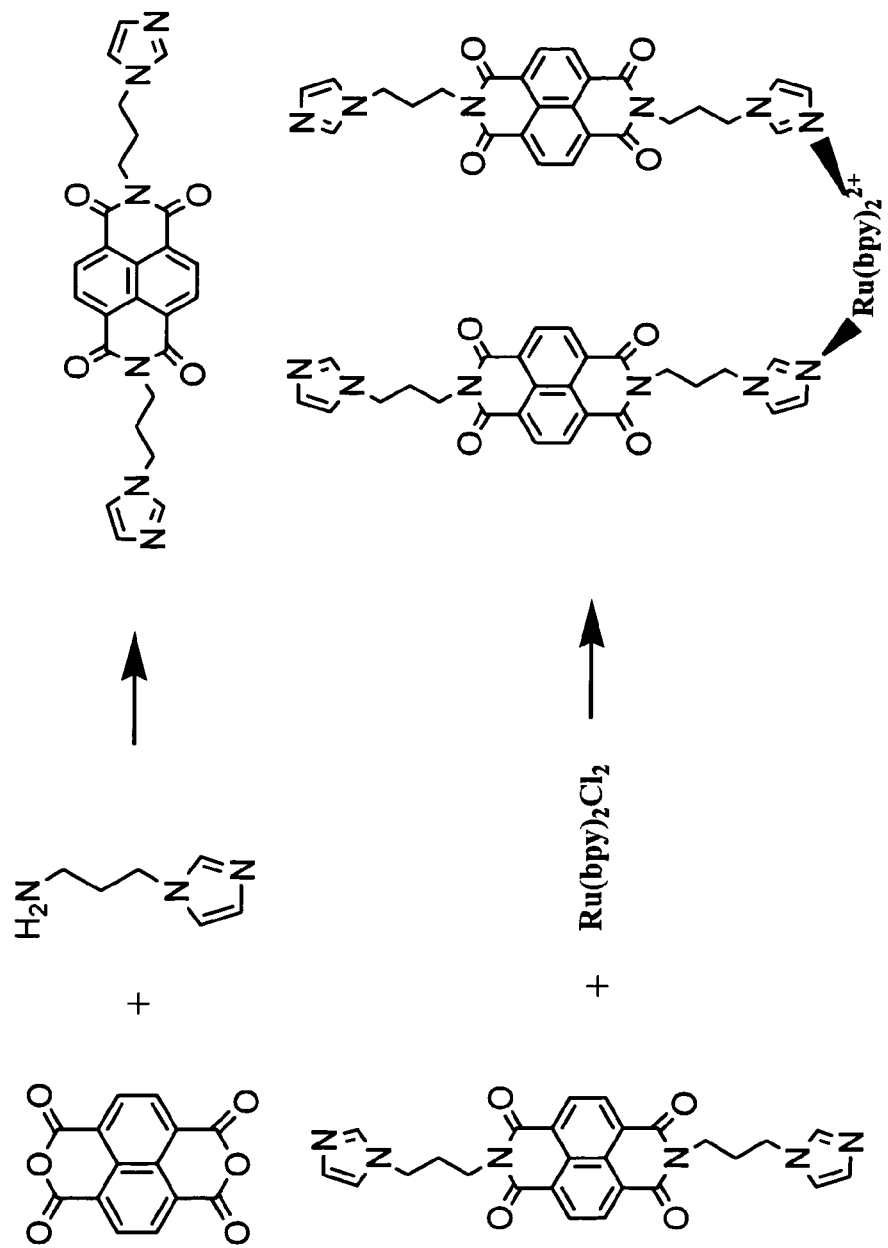
FIG. 1 displays a reaction scheme for preparing a threading intercalator of formula VII.

The detectable group in the threading intercalator comprises, for example, an electrochemical, a catalytic, a chemiluminescent or an electrochemiluminescent detectable group.

By electrochemical detectable group is meant that the group is redox active, and that its presence can be detected electrochemically, for example through voltammetry.

By catalytic detectable group is meant that the group electro-catalytically oxidizes bases in DNA (e.g. guanine), and its presence can be detected voltammetrically.

By chemiluminescent detectable group is meant that the group, when excited chemically, e.g. by the addition of $H_2O_2$, emits a detectable luminescence. Such a group can also be referred to as being photoresponsive.

By electrochemiluminescent detectable group is meant that the group is both redox active and photoresponsive, such that when activated chemically or electrochemically, e.g. through voltammetry or controlled potential electrolysis, the detectable group emits a luminescence and displays a difference in voltametric peak current.

The detectable group can be, for example, a group of formula II:

wherein M represents a metal selected from the group consisting of Ru, Fe, Co Cu and Os. The oxidation state of the metal can be, for example, +2, +3 or +4. Examples of suitable detectable groups include $Ru(bpy)_2^{2+}$ and $Os(bpy)_2^{2+}$.

L in formula II represents a ligand, which can be, for example, a $C_5$-$C_{30}$ heterocyclic group comprising from 1 to 6 heteroatoms selected from the group consisting of N, O, S and P, which heterocyclic group is optionally substituted, for example, by 1 to 6 groups selected from the group consisting of $C_1$-$C_6$ alkyl, $C_2$-$C_6$ alkene, and halogen. Specific examples of suitable ligands include bipyridine, biimidazole, 1,10-phenanthroline or dipyridophenazine.

The number of ligand moieties in the detectable group (represented by the variable n' in formula II), is dependent on the respective natures of the ligand and the metal. More specifically, the number of ligands will be dependent on the steric bulk of the ligand, and the atomic radii of the metal.

Intercalating Groups $IG^1$, $IG^2$ and $IG^3$, which represent the intercalating groups of the threading intercalator of formula I, comprise planar polyaromatic groups (i.e. two or more ring structures). Examples of suitable intercalating groups include, among others, pyridocarbazole, dipyridophenazine, naphthalene imide derivatives and naphthalene diimide derivatives.

Suitable naphthalene imide derivatives include those of formula III:

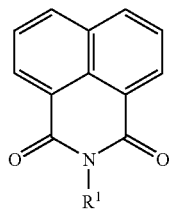

(III)

where the group $R^1$ is selected so that it is capable of forming a coordinative bond with the detectable group.

Suitable naphthalene diimide derivatives include those of formula V:

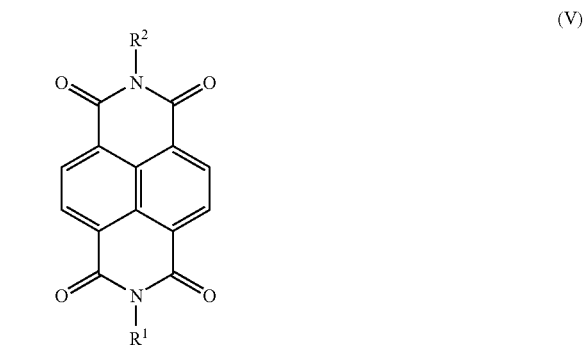

(V)

wherein the group $R^1$ is again selected so that it is capable of forming a coordinative bond with the detectable group, and the group $R^2$ is used to modify the intercalation properties of the threading intercalator.

In one embodiment, $R^1$ is a group of formula IV:

(IV)

wherein $R^6$ is a branched or unbranched, saturated or unsaturated $C_1$-$C_{10}$ alkylene; or a branched or unbranched, saturated or unsaturated $C_1$-$C_{10}$ heteroalkylene having from 1 to 3 heteroatoms selected from the group consisting of N, O, S and P; and AG is a 5 to 10-membered saturated or unsaturated heterocyclic group having from 1 to 3 heteroatoms selected from the group consisting of N, O, S and P. Examples of suitable AG groups include pyridinyl, bipyridinyl, imidazolyl or biimidazolyl.

In one embodiment, $R^2$ can represent —H, —$NR^3R^4$, —$CONR^3R^4$, —$COOR^5$, an optionally branched $C_1$-$C_{10}$ alkyl or an optionally branched $C_2$-$C_{10}$ alkene, which $C_1$-$C_{10}$ alkyl and $C_2$-$C_{10}$ alkene are optionally substituted by one or more substitutents selected from the group consisting of (i) a 5 to 10 membered heterocyclic group having from 1 to 3 heteroatoms selected from the group consisting of N, O, S, and P; (ii) a $C_5$-$C_{14}$ saturated or unsaturated cyclic group; (iii) a $C_6$-$C_{14}$ aryl group; (iv) $NR^3R^4$; (V) $CONR^3R^4$; and (vi) $COOR^5$. The groups $R^3$, $R^4$ and $R^5$ are independently selected from the group consisting of H, $C_1$-$C_6$ alkyl and $C_2$-$C_6$ alkene. In addition, when an $R^2$ group contains a nitrogen atom, the $R^2$ group can optionally form a salt, for example with a halogen. Specific examples of $R^2$ groups include —$(CH_2)_3$-imidazole, —$NH_2$, —$CO_2H$, —$CH_3$, —$(CH_2)_2N(CH_3)_2$, —$(CH_2)_4CH(NH_2)(CONH_2)$, —CH(CONH-adamantyl) $(CH_2)_4NH_2$, —$CH(CH_3)$ $(CH_2)_3N(C_2H_5)_2$, —$(CH_2)N(CH_3)_2$, —$(CH_2)N^+(CH_3)_3I^-$, —$(CH_2)_3N(CH_3)_2$, —$(CH_2)_4(CH)(CONH_2)(NH_2)$, —$CH(CONH_2)(CH_2)_4NH_2$, —CH(CONH-adamantyl)$(CH_2)_4NH_2$, —$CH(CH_3)(CH_2)_3N(C_2H_5)_2$, and —$CH(CH_3)$ $(CH_2)_3N^+(C_2H_5)_2$ $(CH_3)I^-$.

Analytical Applications

Processes for detecting the presence of specific DNA fragments using a threading intercalator are described in EP 1 065 278, and the relevant portions of this reference are incorporated herein by reference.

The threading intercalators can be used to detect the presence of specific single stranded nucleic acid molecules in an oligo- or polynucleic acid sample. In one embodiment, a sample of single stranded oligo- or poly-nucleotide molecules is contacted with nucleotide acid molecule probes which are immobilized onto an electrode substrate. Once the probe molecules and the corresponding nucleotide molecules in the oligo- or poly-nucleotide sample have been hybridized, a threading intercalator as described herein is introduced, and the threading intercalator preferentially intercalates into the double stranded hybrid now fixed onto the electrode substrate. Using methods appropriate to the detectable group found in the threading intercalator, the presence of double stranded nucleotide molecules on the electrode substrate can be detected.

The process can also be carried out in a single step, where the threading intercalator is introduced prior to hybridization. As the threading intercalator preferentially intercalates double stranded nucleic acid molecules, intercalation will only take place once the probe molecules have hybridized with corresponding single stranded nucleic acid molecules found in the oligo or poly-nucleotide sample.

For redox active detectable groups, the presence of the nucleotides on the electrode can be detected by observing differences in voltametric peak current which would be caused by the presence of the redox active group in the intercalator. For photoresponsive groups, the presence of the nucleotides on the electrode can be detected by observing luminescence caused by the application of a light source onto the electrode substrate. For electrochemiluminescent detectable group, the presence of the nucleotide of the electrode can be determined by activating the electrode by either passing a current or applying a light source, and then observing differences in voltametric peak current or observing luminescence. Preferably, the electrochemiluminescent detectable group is activated by applying a current to the electrode and then observing the electrode for any luminescent emissions.

Examples of suitable electrode materials include, for example, gold, platinum, stainless steel, indium-tin oxide film coated glass, and carbon-based materials. For photoresponsive threading intercalators, a conducting material is preferably used as an electrode.

Examples of solvents suitable for carrying out the hybridization of the probe molecules with the single stranded nucleic acid molecules include, for example, tri-n-propylamine (TPA).

The following examples are provided to illustrate the invention. It will be understood, however, that the specific details given in each example have been selected for purpose of illustration and are not to be construed as limiting the scope of the invention. Generally, the experiments were conducted under similar conditions unless noted.

EXAMPLES

Chemicals

1(3-aminopropyl)-imidazole (AI, 98%,) and 1,4,5,8-naphthalene tetracarboxylic dianhydride (NTD, >95%) were purchased from Sigma-Aldrich (St Louis, Mo., USA). Ru(bpy)$_2$Cl$_2$ (99%) was obtained from Avocado Research Chemicals Ltd (Leysham, Lancester, UK). All other reagents were obtained from Sigma-Aldrich and used without further purification. Oligonucleotide capture probes (CPs) used were custom-made by Alpha-DNA (Montreal, Canada) and all other oligonucleotides were custom-made by 1st Base Pte Ltd (Singapore). A 10 mM Tris-HCl-1.0 mM EDTA-0.10 M NaCl buffer solution (TE) was used as hybridization buffer. A phosphate-buffer saline (PBS, pH 7.4), consisting of 0.15 M NaCl and 20 mM phosphate buffer, was used as the supporting electrolyte.

Instruments

Electrochemical experiments were carried out using a CH Instruments model 660A electrochemical workstation coupled with a low current module (CH Instruments, Austin, Tex.). A conventional three-electrode system, consisting of a 3.0-mm-diameter gold working electrode, a nonleak-miniature Ag/AgCl reference electrode (Cypress Systems, Lawrence, Kans.), and a platinum wire counter electrode, was used in all electrochemical measurements. To avoid the spreading of the sample droplet beyond the 3.0-mm diameter working area, a patterned hydrophobic film was applied to the gold electrode after the immobilization of the CP. All potentials reported in this work were referred to the Ag/AgCl electrode. UV-visible spectra were recorded on an Agilent 8453 UV-visible spectrophotometer. Mass spectrometric experiments were performed with a Finnigan/MAT LCQ Mass Spectrometer (ThermoFinnigan, San Jose, Calif.). All spectra were recorded at room temperature unless otherwise noted.

Measurements of electrochemiluminescence were performed with a Fluorolog®⁻3 spectrofluorometer (JobinYvon Inc, Edison, N.J.) in conjunction with the 660A electrochemical workstation. The three-electrode system consisted of a gold working electrode, a nonleak-miniature Ag/AgCl reference electrode (Cypress Systems, Lawrence, Kans.) and a platinum foil counter electrode. The three electrodes were hosted in a standard fluorescence cuvette and arranged in such a way that the working electrode faces the detection window and the other two electrodes are behind the working electrode temperature. All potentials reported in this work were referred to the Ag/AgCl electrode. All experiments were carried out at room temperature, unless otherwise stated.

Example 1

Synthesis of ND-Ru-ND

Formation of ND-Ru-ND

The general synthesis steps for preparing ND-Ru-ND are outlined in FIG. 1.

Figure 2A:
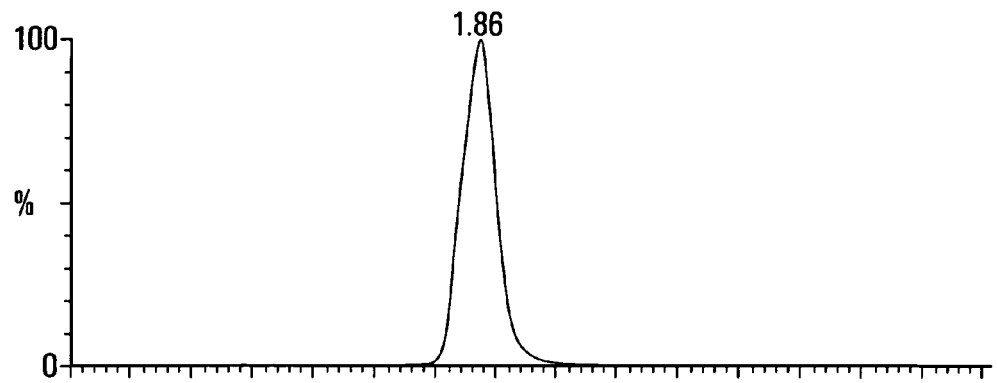
FIG. 2 shows the reverse-phase HPLC (A) and MS (B) results of purified ND-Ru-ND (C18 column, eluent: $H_2O$, MS detection mode: ESI).
Figure 2B:
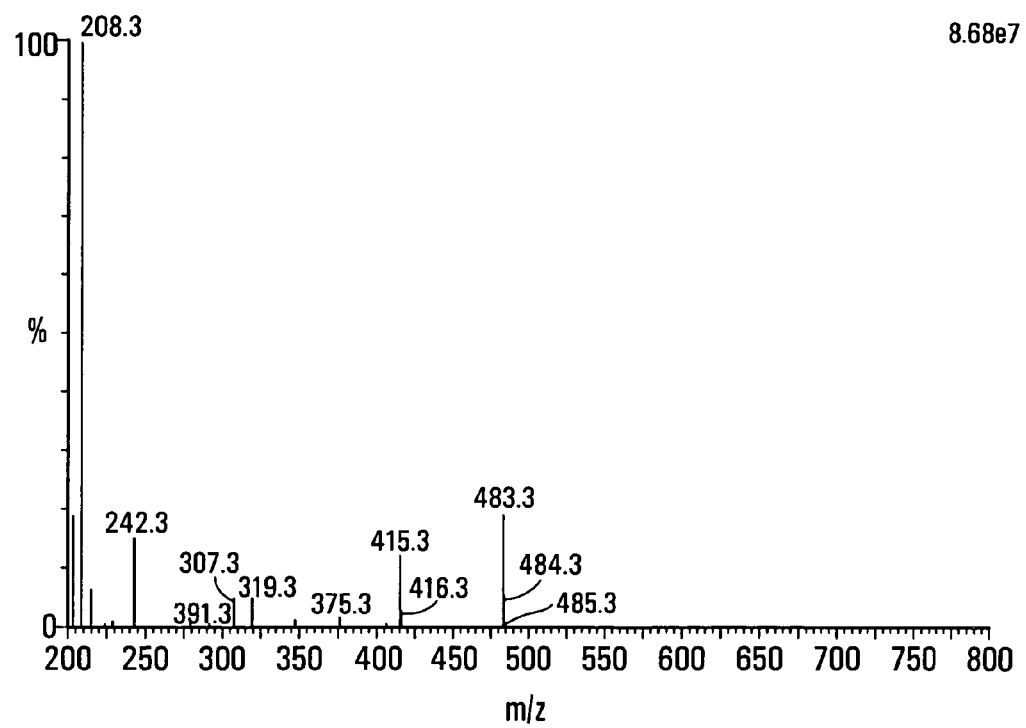

ND was first prepared following a general procedure for the synthesis of diimide (Rademacher et al., *Chem. Ber.* 1982, 115, 2972-2976; and Katz et al., *J. Am. Chem. Soc.* 2000, 122, 7787-7792). Briefly, to a magnetically stirred mixture of 3.0 ml of 1(3-aminopropyl)-imidazole (AI) and 3.0 ml of tetrahydrofuran was slowly added 0.30 g of naphthalene tetracarboxylic dianhydride (NTD). The rate of addition was controlled so that there was little clogging. The reaction mixture was refluxed for 24 h and then cooled to room temperature. Next, it was dispersed in 10 ml of acetone/water (3/1) mixture and poured into 500 ml of rapidly stirred anhydrous ether to precipitate the compound. The precipitate was collected by suction filtration through a fine fritted funnel and washed briefly with ethanol. Purification was performed by crystallization from chloroform/ethanol (1/1 by volume) and dried under vacuum at 40° C. overnight to give 0.46 g of yellow crystals (yield 85%). 1H NMR (300 MHz CDCl$_3$) δ 8.76 (4H), 7.54 (2H), 7.26 (2H), 4.27 (4H), 4.12 (4H), 2.31 (4H) and 1.83 9(2H). Reverse-phase HPLC-MS tests showed that the desired compound had been successfully synthesized and that the purity of the compound is >99%, as indicated by a single elution peak at 1.68 min and an m/z of 483.3 (FIG. 2).

Nd—Ru-ND was synthesized in a single-step double ligand-exchange reaction. To a solution of Ru(bpy)$_2$Cl$_2$ (0.10 g, 0.20 mmol) in 8.0 ml fresh-distilled ethylene glycol was added ND (0.24 g, 0.50 mmol) in small portions over 10 min and the resulting mixture was refluxed for 30-40 min. The completion of the ligand-exchange reaction was monitored by cyclic voltammetry. The orange reaction mixture was then poured slowly into 500 ml of rapidly stirred anhydrous ether. The precipitate was collected by suction filtration through a fine fritted funnel. The crude product was dissolved in 8.0-10 ml of water extracted twice with chloroform. The precipitate was further purified by crystallization from ethanol giving the pure product in 75% yield. The product showed a single pair of reversible redox waves at a gold electrode with an $E_{1/2}$ of 0.68 V in PBS. To ensure a complete double ligand-exchange, slight excess of ND (20-25%) was required.

Figure 3:
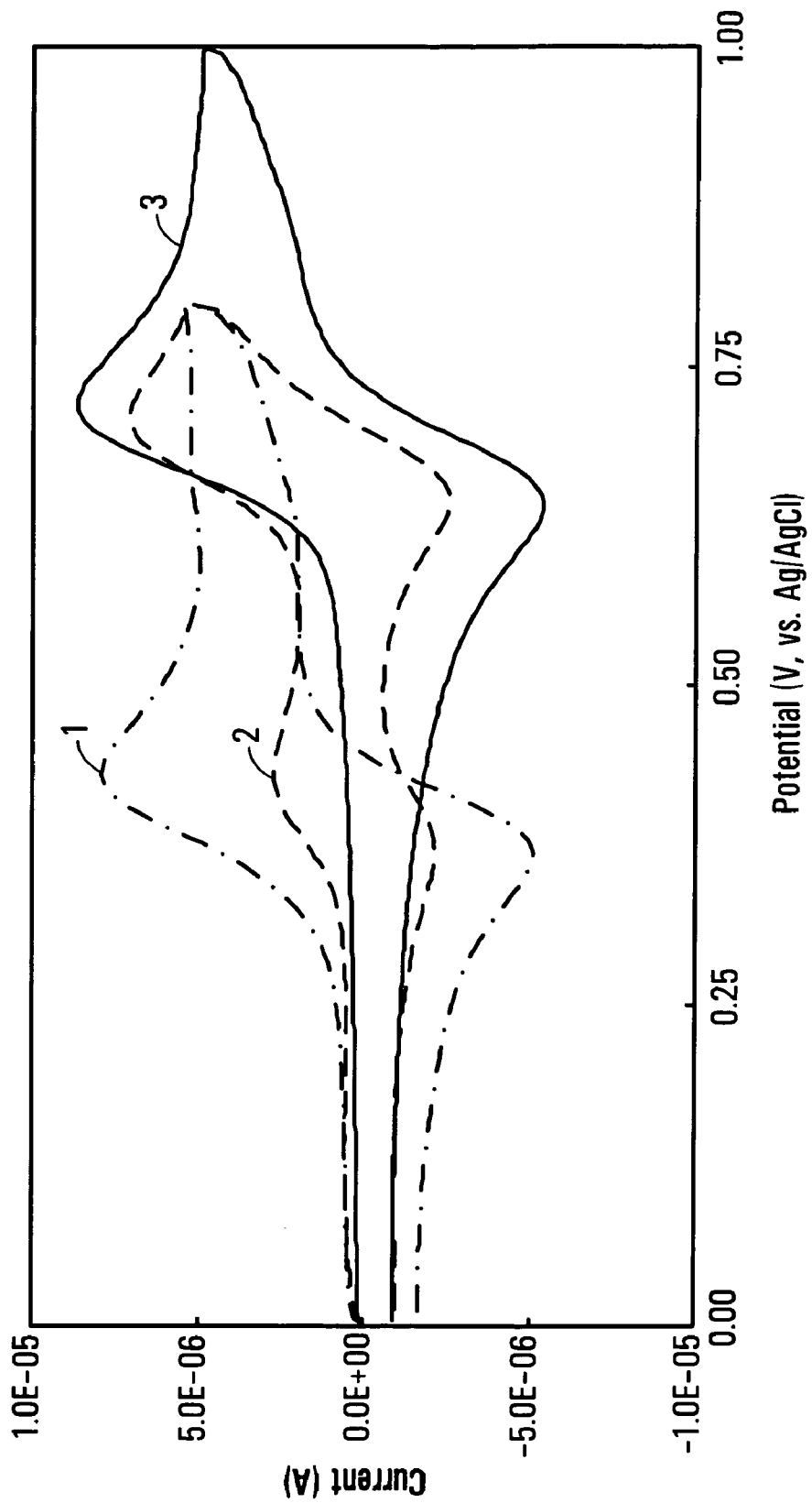
FIG. 3 shows normalized cyclic voltammograms of $Ru(bpy)_2Cl_2$ after (1) 5 and (2) 20 min of refluxing with ND in ethylene glycol and (3) purified Nd—Ru-ND (Supporting electrolyte for (3) PBS, potential scan rate 100 mV/s).

The formation of ND-Ru-ND can be conveniently monitored by cyclic voltammetry. During reflux in ethylene glycol, cyclic voltammetric tests were conducted every 5 min. FIG. 3 shows two typical voltammograms obtained in the first 40 min. Before adding ND to Ru(bpy)$_2$Cl$_2$, one pair of reversible voltammetric peaks centered at 0.40 V were obtained, corresponding to the well-known redox process of Ru(bpy)$_2$Cl$_2$. Upon adding ND, a new pair of voltammetric peaks appeared at 0.68 V, indicating the formation of ND-Ru-ND (FIG. 3 trace 1 and 2). Both electron transfer processes are clearly resolved and have all the characteristics of reversible processes, except the slightly larger peak-to-peak potential separations, which are mainly due to a higher iR drop of the reaction medium. The intensities of the voltammetric peaks at 0.68 V increased gradually with reaction time. Simultaneously, those at 0.40 V diminished gradually. Minute voltammetric peaks at 0.40 V were obtained after 40 min of refluxing and they remained unchanged after prolonged refluxing, indicating that the reaction had reached its equilibrium. Voltammetric tests of the thus purified ND-Ru-ND showed only one pair of voltammetric peaks implying that the purification process is very effective (FIG. 3 trace 3).

Figure 4:
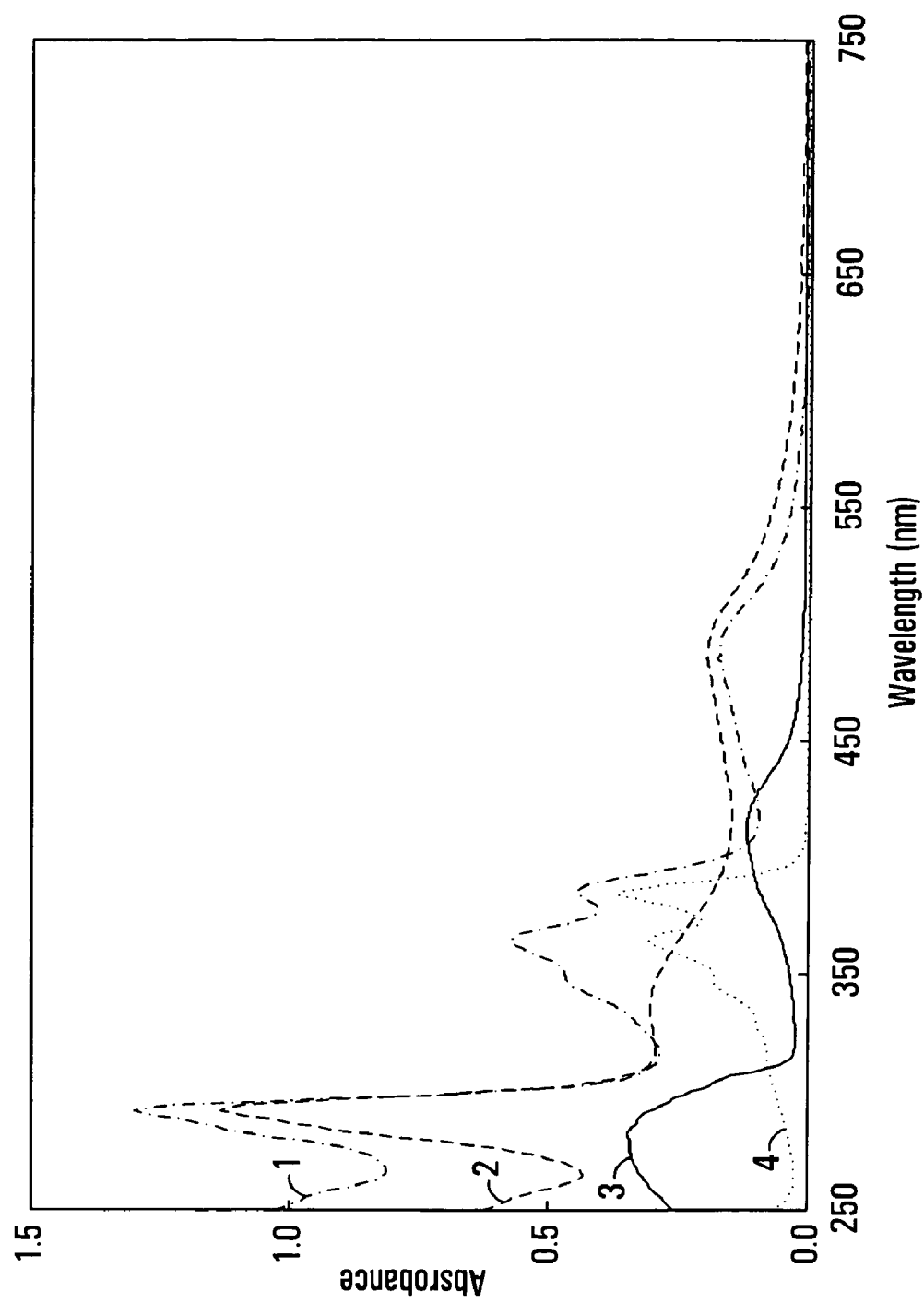
FIG. 4 shows UV-vis absorbance spectras of (1) 25 μM ND-Ru-ND, (2) 25 μM $Ru(bpy)_2(Im)_2$, (3) 25 μM $Ru(bpy)Cl_2$ and (4) 50 μM ND in ethanol.

UV-vis absorbance spectra of the starting materials, a Ru(bpy)$_2$(Im)$_2$ (Im=imidazole) model compound and ND-Ru-ND are depicted in FIG. 4. The UV-vis spectrum of ND-Ru-ND (FIG. 3 trace 1) is similar to that of Ru(bpy)$_3$-naphthalene diimide compound. It exhibits an intense band in the UV region due to intraligand (IL)$\delta \rightarrow \delta$*(bpy) transitions and by a broad band in the visible region (400-600 nm) due to spin allowed Ru(d$\pi$)$\rightarrow$bpy($\pi$*) metal-to-ligand charge-transfer (MLCT) transition; the peaks at 380 and 361 nm are mainly due to $\pi \rightarrow \pi$* transition in ND with some contribution from underlying MLCT absorbance. The absorption maximum of ND-Ru-ND is red-shifted with respect to Ru(bpy)$_2$Cl$_2$, from 415 to 495 nm (FIG. 3 trace 3). Same changes were also observed in the spectrum of the model compound Ru(bpy)$_2$(Im)$_2$ as compared to Ru(bpy)$_2$Cl$_2$ (FIG. 4 trace 2). This is likely a direct consequence of the ligand exchange which results in two types of MLCT transitions within the ruthenium complex: Ru*$\rightarrow$bpy, and Ru*$\rightarrow$AI. The imidazole groups of ND are conjugated, resulting in a lower $\pi$* level for this ligand relative to the chloride of the complex. Moreover, the spectrum of ND-Ru-ND is a composite of the absorbance spectra from both the ND moiety and the Ru(bpy)$_2$(Im)$_2$ complex (Traces 1, 2 and 4). A simple overlay of Ru(bpy)$_2$(Im)$_2$ and ND generated a spectrum which is almost identical to that of ND-Ru-ND, confirming the formation of ND-Ru-ND.

The UV-vis spectrophotometric and electrochemical evidence shows that the coupling between ND and Ru(bpy)$_2$Cl$_2$ results in a coordinative linkage and that two ND molecules are grafted onto Ru(bpy)$_2$. A more direct proof of the formation of ND-Ru-ND was provided through a series of mass spectrometric tests on ND-Ru-ND using electron-spray ionization mass spectrometry (ESI-MS). Predominant peaks were found at m/z 689, 483.3, 460, and 242.3, corresponding to (ND-Ru-ND)$^{2+}$/2, (ND+H$^+$), (ND-Ru-ND+H$^+$)$^{3+}$/3, and (ND+2H$^+$)/2, respectively (Table 1), which are in good agreement with the molecular weights of the desired compounds. Since mono-grafted Ru(bpy)$_2$ was not observed in the ESI-MS spectrum, incomplete grafting of Ru(bpy)$_2$ can be ruled out.

TABLE 1

ESI-MS spectrometric dada of ND-Ru-ND

| m/z | Relative intensity (%) | Identity |
|---|---|---|
| 242.3 | 100 | (ND + 2H$^+$)/2 |
| 460 | 30 | (ND-Ru-ND + H$^+$)$^{3+}$/3 |
| 483.3 | 22 | (ND + H$^+$) |
| 689 | 62 | (ND-Ru-ND)$^{2+}$/2 |

Electrochemical Properties of ND-Ru-ND

As illustrated in trace 3 of FIG. 3, ND-Ru-ND behaved exactly as expected for a highly reversible redox couple in solution. Little change was observed after numerous repetitive potential cycling between 0.0 V and +1.0 V, revealing a good stability of ND-Ru-ND in solution. At slow scan rates, <1.0 V mV/s, a typical diffusion-controlled voltammogram was recorded as expected for a one-electron exchange system exhibiting an ideal Nernstian behavior: the peak current is proportional to the square root of the potential scan rate, the peak-to-peak potential separation is very close to the theoretical value of 59 mV and potential scan rate independent. Such results ascertain that all of the ruthenium redox centers are allowed to reach the electrode surface and proceed to reversible heterogeneous electron transfer.

Intercalation with DNA

Figure 5A:
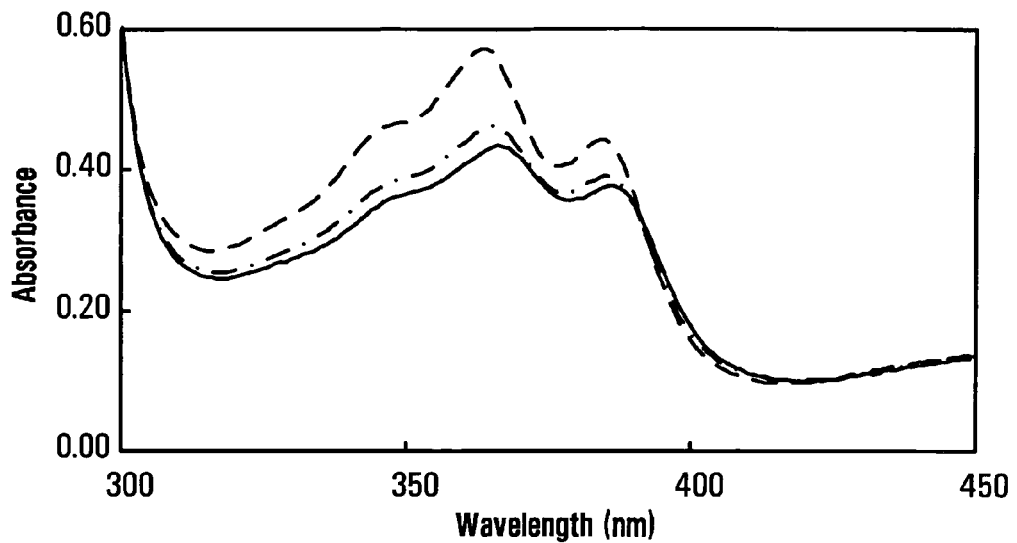
FIG. 5 shows (A) a UV-vis spectra of 20 μM ND-Ru-ND as a function of increasing concentration of salmon sperm DNA (in base pair) of (1) 0, (2) 40 and (3) 100 μM; and (B) a Scatchard plot for the titration of a hairpin oligonucleotides/EB (5.0 μM/8.0 μM) mixture with ND-Ru-ND.
Figure 5B:
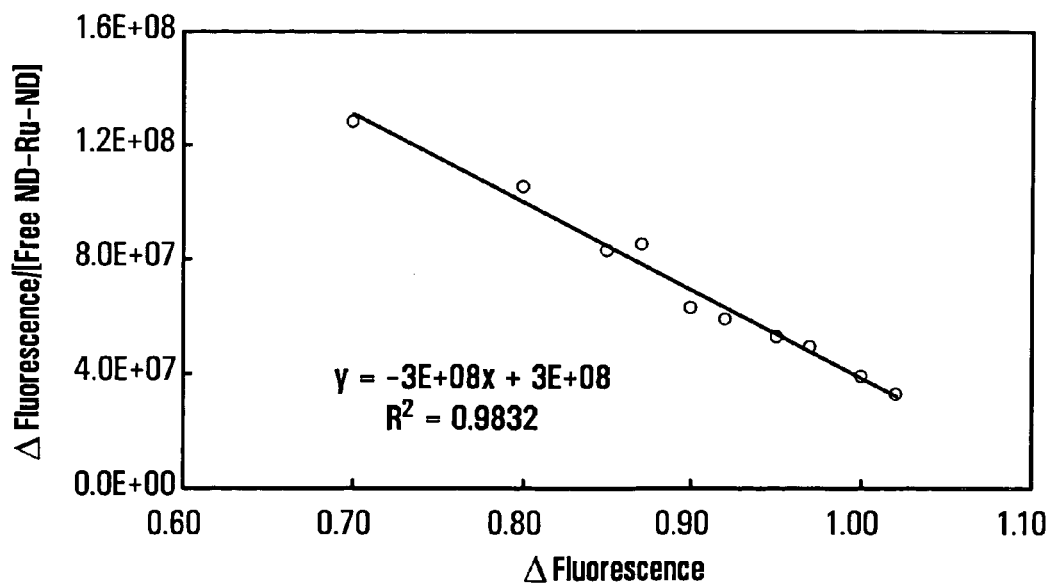

It was found that ND-Ru-ND intercalates very strongly to ds-DNA. To determine the mode of interaction of ND-Ru-ND with ds-DNA, UV-vis spectrophotometry of ND-Ru-ND in the presence of increasing amounts of salmon sperm DNA was investigated. In the UV-vis spectrophotometry, signatures of intercalative binding, where the fused planar aromatic ring system of a threading intercalator inserts itself between the base pairs of ds-DNA, are hypochromism and red shifts. As shown in FIG. 5A, addition of DNA to ND-Ru-ND at a DNA base pair/ ND-Ru-ND ratio of 6.0 resulted in a 40% decrease and a 3-nm-red-shift of the ND absorbance band at 364 and 385 nm. Similar phenomena were previously observed with ND having aliphatic tertiary amine side molecules. The ND absorbance band hypochromism reached a plateau at the base pair/ND-Ru-ND ratio>7.0, and a constant hypochromism was observed for ratios above 7.0, indicating that binding of ND-Ru-ND to ds-DNA takes place by preferential intercalation of the ND. To have a better estimation of the intercalating property, a competition experiment, similar to that proposed by Boger (Boger et al., *J. Am. Chem. Soc.* 2001, 123, 5878-7891) was designed using short hairpin oligonucleotides. The basis of this methodology involves the use of two intercalators, one fluorescent and one non-fluorescent. The fluorescent intercalator first saturates the ds-DNA, then a second intercalator, in this case ND-Ru-ND, is introduced into the system with gradual increase in concentration. It was hypothesized that the two intercalators would bind to similar sites in the ds-DNA. For the competition experiment, changes in fluorescent intensity were monitored during the displacement of ds-DNA-bound fluorescent molecules by ND-Ru-ND through an increasing concentration of ND-Ru-ND molecules in the system. A well known threading intercalator, ethidium bromide (EB), was chosen as the fluorescent indicator. EB displays a 25-fold fluorescence enhancement upon binding to ds-DNA, which provides sufficient sensitivity and good discrimination against free EB molecules in fluorescent measurement. In addition, the kinetics of EB intercalation is quite fast, which significantly shortens the time needed to reach equilibrium. To ensure that the approach was appropriate for this study, an increasing concentration (0-100 µM) of a well-studied non-fluorescent intercalator (ND) was first added to the EB saturated ds-DNA solution. Gel electrophoretic experiments showed that the fluorescent intensity of the EB intercalated with ds-DNA diminished gradually as the concentration of ND increased. The binding constant, $K_d$ of $8.1 \times 10^5$, estimated from the experimental data, was in good agreement with value known in the literature (Murr et al., *Bioorg. Med. Chem.* 2001, 9, 1141-1446). Subsequently, ND-Ru-ND was studied with respect to its ability to compete against EB for binding to ds-DNA using the same approach. As shown in FIG. 5B, ND-Ru-ND exhibited a remarkable binding affinity towards ds-DNA. The binding constant $K_d$, estimated from the experimental data, was $3.0 \times 10^8$, corresponding to approximately a 370-fold enhancement over ND. Without wishing to be bound by theory, it is believed that the stability constant enhancement is due in part to the simultaneous intercalations of the two ND groups, which increase the stability of the DNA/ND-Ru-ND adduct. In addition, after the ND groups have intercalated with ds-DNA, the dicationic $Ru(bpy)_2$ group in ND-Ru-ND may form an ion-pair with phosphates of ds-DNA, making the two intercalated ND groups more tightly fixed between the base pairs of ds-DNA.

ECL Behavior of ND-Ru-ND in TPA Solution

Figure 6B:
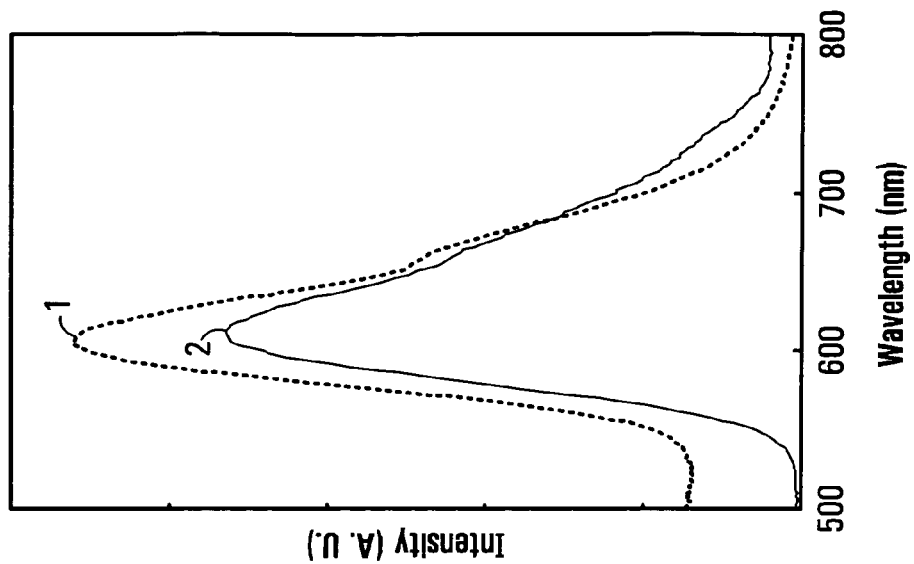
FIG. 6 shows (A) ECL intensity versus potential profiles along with the cyclic voltammogram obtained in a pH 9.0 phosphate buffer containing 5.0 μM ND-Ru-ND and 0.20 M TPA (Potential scan rate 20 mV/s0); and (B) (1) a photoluminescence spectrum of ND-Ru-ND (430 nm illumination) in a pH 9.0 phosphate buffer and (2) an ECL spectrum of ND-Ru-ND obtained in pH 9.0 phosphate buffer containing 10 μM ND-Ru-ND +0.20 M TPA (for clarity, the voltammogram of ND-Ru-ND was scaled up 50 times).
Figure 6A:
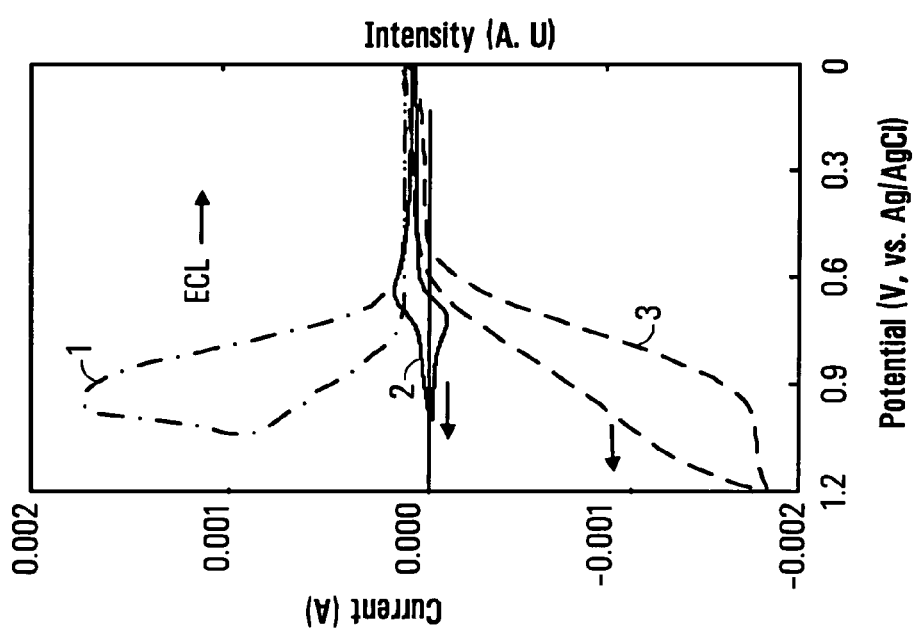

The cyclic voltammetric and ECL responses of 5.0 µM ND-Ru-ND in pH 9.0 phosphate buffer containing 0.20 M TPA co-reactant at a platinum electrode are depicted in FIG. 6. As shown in FIG. 6A, the onset potential for ND-Ru-ND oxidation and for ECL is ~0.60 V. The peak potential for the oxidation of TPA occurred at 1.0 V (FIG. 6A trace 3) while that of ND-Ru-ND occurred at 0.68 V (FIG. 6A trace 2), implying that the oxidation of ND-Ru-ND at the electrode surface occurs before that of TPA is required for the production of the excited state, $Ru(bpy)_2^{2+*}$ and ECL. In addition, some catalytic effect was observed on the oxidation of TPA in the presence of ND-Ru-ND. Maximum ECL intensity for this system was observed at 0.94 V (FIG. 6A trace 1). As expected, within experimental error, the ECL spectra obtained for ND-Ru-ND at different positive potential biases had the same features as the photoluminescence spectrum of ND-Ru-ND in phosphate buffer, because the emission is the result of the decay of the same MLCT excited state $Ru(bpy)_2^{2+*}$, generated by either illumination or electrochemical excitation. FIG. 6B shows the ECL spectrum of ND-Ru-ND compared with its photoluminescence spectrum.

Example 2

Immobilization of CP on Gold Electrode

The preparation and pretreatment of gold electrodes was carried out as previously described in the literature. Briefly, prior to capture probe adsorption, a gold electrode was exposed to oxygen plasma for 5-10 min and then immediately immersed in absolute ethanol for 20 min to reduce the oxide layer. A CP monolayer was adsorbed by immersing the gold electrode in a PBS solution of 100 µg/ml CP for 16-24 hours. After adsorption, the electrode was copiously rinsed with PBS and soaked in PBS for 20 min, rinsed again, and blown dry with a stream of air. The surface density of CP, assessed electrochemically by the use of cationic redox probe according to the procedure proposed by Steel (Steel et al., *Anal. Chem.* 1998, 70, 4670-4677), was found to be in the range of $1.13-1.30 \times 10^{-11}$ mol/cm$^2$. To minimize non-DNA related PIND-Os uptake and improve the quality and stability of the CP monolayer, the CP-coated gold electrode was immersed in an ethanolic solution of 2.0 mg/ml 1-mercaptododecane (MD) for 4-6 h. Unreacted MD molecules were rinsed off and the electrode was washed by immersion in a stirred ethanol for 10 min and followed by thorough rinsing with ethanol and water. The electrode was ready after air-dry.

Example 3

Hybridization and Detection

Figure 8:
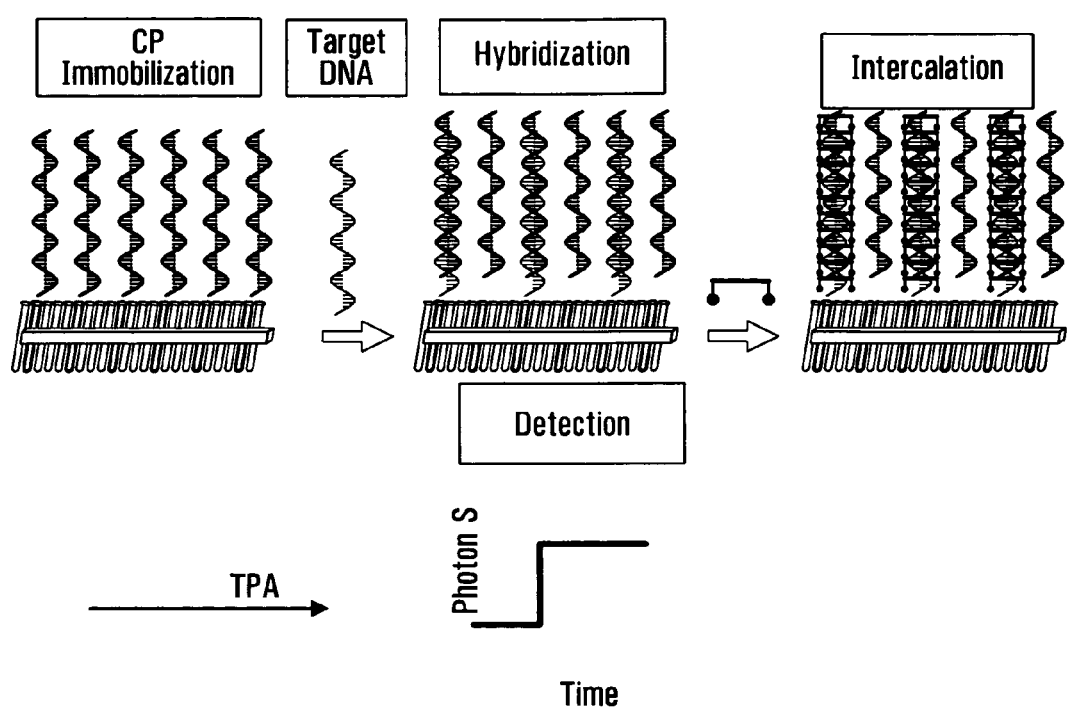
FIG. 8 depicts a scheme for the hydbridization of DNA and its electrochemical detection using a bidentate threading intercalator.

The hybridization of a target DNA and its electrochemical detection were carried out in three steps, as depicted in FIG. 8. First, the CP coated electrode was placed in a moisture saturated environmental chamber maintained at 60° C. A 2.5 µl aliquot of hybridization solution containing the target DNA was uniformly spread onto the electrode (low stringency, 27° C. below the salt-adjusted melting temperature). It was then rinsed thoroughly with a blank hybridization solution at 60° C. after 30-min of hybridization and incubated at 25° C. for 10 min with a 5.0 µl aliquot of 100 µg/ml of ND-Ru-ND in the hybridization solution. ND-Ru-ND was attached to the hybridized target DNA via threading intercalation. It was then air-cooled and held at room temperature for 10 min before being thoroughly rinsed with NaCl-saturated phosphate buffer (pH 7.4) containing 10% ethanol. ECL was measured at 1.0 V in pH 9.0 phosphate buffer containing 0.20 M TPA.

DNA biosensors with redox active moieties as electrochemical indicators have previously been reported (Takenaka, S.; Yamashita, K.; Takagi, M.; Uto. Y.; Kondo, H. *Anal. Chem.* 2000, 72, 1334-1341). When hybridization occurs, the threading intercalator selectively interacted with the ds-DNA and gave a greatly enhanced analytical signal compared to non-hybridized ss-DNA. The difference in voltammetric peak current was thus used for quantitation purposes.

Similarly to redox active intercalators, ND-Ru-ND was firstly evaluated as a novel electroactive tag for possible applications in ultrasensitive DNA sensing. In the first hybridization test, complementary and a non-complementary oligonucleotide were selected as target DNAs. Upon hybridization with the biosensor, the complementary target DNA was selectively bound to its complementary CP and became fixed on the biosensor surface. On the other hand, hybridization with the non-complementary DNA failed to capture any nucleotides, and therefore little change of the biosensor was expected. Thorough rinsing with the hybridization buffer washed off most of the non-hybridization related DNA. ND-Ru-ND was brought to the biosensor surface during a subsequent incubation with a ND-Ru-ND solution. Linear scan voltammograms for the biosensors after hybridization with the complementary and non-complementary target DNAs are shown in FIG. 7A. For the non-complementary DNA, after hybridization a minute voltammetric peak was observed at the redox potential of ND-Ru-ND (FIG. 7A trace 1), largely due to pure electrostatic interaction of ND-Ru-ND and CP on the biosensor surface. As shown in traces 2 in FIG. 7A, after hybridization with the complementary target DNA, a slight positive shift in the redox potential was observed and the peak current increased by as much as 100-fold. It was found that extensive washing with NaCl saturated PBS removed most of the non-DNA related ND-Ru-ND uptake. These results clearly demonstrated that ND-Ru-ND selectively interacts with ds-DNA and the ND-Ru-ND-ds-DNA adduct has a very slow dissociation rate, which paves the way for developing an ultrasensitive DNA biosensor. Consequently, using the intercalated ND-Ru-ND as the electroactive indicator for direct detection of DNA was evaluated. A detection limit of 0.40 nM (0.80 femtomoles) and a dynamic range up to 300 nM were obtained.

The ECL behavior of the hybridized biosensors before and after incubation with ND-Ru-ND were then examined with a positive potential bias of 1.0 V applied to the biosensor in a pH 9.0 phosphate buffer containing 0.20 M TPA. FIG. 7B shows ECL responses of the biosensors after hybridization with the complementary and non-complementary target DNAs and after ND-Ru-ND incubation. Trace 1 in FIG. 7B was obtained with the biosensor hybridized with non-complementary target DNA while trace 2 corresponded to the biosensor hybridized with the complementary DNA. Very little ECL response was observed for the non-complementary target DNA hybridized biosensor, largely due to the presence of a very small amount of electrostatically bound ND-Ru-ND to the DNA. It can be seen that the presence of intercalated ND-Ru-ND in the complementary target DNA hybridized biosensor greatly increase the ECL signal of the system with an enhancement of over 50-fold. The much improved ECL response after ND-Ru-ND intercalation is due to a genuine ECL process of the Ru(bpy)$_2^{2+}$ moieties. It was found that the ECL signal is proportional to the target DNA concentration in the range of 0.80-500 pM with a detection limit of 400 fM, 2000-fold higher that of the direct voltammetric detection of DNA. The ECL data agreed well with the voltammetric results obtained earlier in solution and confirmed again that ND-Ru-ND is electrochemiluminescent and it can be used to detect DNA with high specificity and sensitivity.

All publications, patents and patent applications cited in this specification are herein incorporated by reference as if each individual publication, patent or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a", "an", and "the" include plural reference unless the context clearly dictates otherwise. Unless defined otherwise all technical and scientific terms used herein have the same meaning as commonly understood to one of ordinary skill in the art to which this invention belongs.

The invention claimed is:

1. A threading intercalator of general formula I:

$$IG^1\text{-}DG\text{-}IG^2\text{-}(DG\text{-}IG^3)_n \quad (I)$$

wherein $IG^1$, $IG^2$ and $IG^3$ are the same or different and each of $IG^1$, $IG^2$ and $IG^3$ is an intercalating group that is a naphthalene imide derivative or a naphthalene diimide derivative, with at least one of $IG^1$, $IG^2$ and $IG^3$ being a napthalene diimide derivative having a structure of formula V:

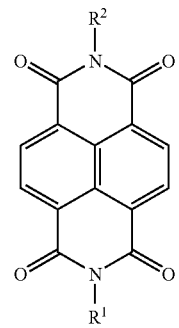

(V)

$R^1$ is a group which is capable of forming a coordinative bond with the detectable group and has a structure of formula IV:

$$—R^6\text{-}AG \quad (IV)$$

wherein $R^6$ is a branched or unbranched, saturated or unsaturated $C_1$-$C_{10}$ alkylene; or a branched or unbranched, saturated or unsaturated $C_1$-$C_{10}$ heteroalkylene having from 1 to 3 heteroatoms selected from the group consisting of N, O, S and P; and AG is a saturated or unsaturated 5 to 10-membered heterocyclic group having from 1 to 3 heteroatoms selected from the groups consisting of N, O, S and P;

$R^2$ is H, $NR^3R^4$, $CONR^3R^4$, $COOR^5$, an optionally branched $C_1$-$C_{10}$ alkyl or an optionally branched $C_2$-$C_{10}$ alkene, which $C_1$-$C_{10}$ alkyl and $C_2$-$C_{10}$ alkene are optionally substituted by one or more substituents selected from the group consisting of (i) a 5 to 10 membered heterocyclic group having from 1 to 3 heteroatoms selected from the group consisting of N, O, S, and P; (ii) a $C_5$-$C_{14}$ saturated or unsaturated cyclic group; (iii) a $C_6$-$C_{14}$ aryl group; (iv) $NR^3R^4$; (v) $CONR^3R^4$; and (vi) $COOR^5$;

$R^3$, $R^4$ and $R^5$ are each independently selected from the group consisting of H, $C_1$-$C_6$ alkyl and $C_2$-$C_6$ alkene, and when the $R^2$ group contains a N atom, $R^2$ optionally forms a salt;

DG is a catalytic, electrochemical, a chemiluminescent or an electrochemiluminescent detectable group having a structure of formula II:

$$-M[(L)_{n'}]- \quad (II)$$

wherein

M represents a metal selected from the group consisting of Ru, Fe, Co, Cu and Os;

L is a coordinative binding ligand that is a $C_5$-$C_{30}$ heterocyclic group comprising from 1 to 6 heteroatoms selected from the group consisting of N, O, S and P, optionally substituted by 1 to 6 groups independently selected from $C_1$-$C_6$ alkyl, $C_2$-$C_6$ alkene and halogen; and n' is an integer from 1 to 6; and n is 0 or 1.

2. The threading intercalator according to claim 1, wherein n is 0.

3. The threading intercalator according to claim 1, wherein the detectable group is electrochemiluminescent.

4. The threading intercalator according to claim 1, wherein the metal has an oxidation state of +2, +3 or +4.

5. The threading intercalator according to claim 1, wherein the ligand is bipyridine, biimidazole, 1,10-phenanthroline or dipyridophenazine.

6. The threading intercalator according to claim 1, wherein the ligand is bipyridine.

7. The threading intercalator according to claim 1, wherein the detectable group is Ru(bipyridine)$_2^{2+}$.

8. The threading intercalator according to claim 1, wherein the naphthalene imide derivative has a structure of formula III:

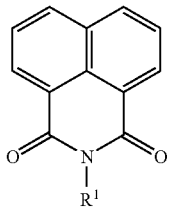

(III)

wherein R$^1$ is as defined in claim 1 for formula V and is independently selected from R$^1$ in formula V.

9. The threading intercalator according to claim 1, or claim 8 wherein AG in formula V or formula III is pyridinyl, bipyridinyl, imidazolyl or biimidazolyl.

10. The threading intercalator according to claim 1, wherein R$^2$ is —(CH$_2$)$_3$-imidazole, —NH$_2$, —CO$_2$H, —CH$_3$, —(CH$_2$)$_2$N(CH$_3$)$_2$, —(CH$_2$)$_4$CH(NH$_2$)(CONH$_2$), —CH(CONH-adamantyl)(CH$_2$)$_4$NH$_2$, —CH(CH$_3$)(CH$_2$)$_3$N(C$_2$H$_5$)$_2$, —(CH$_2$)N(CH$_3$)$_2$, —(CH$_2$)N$^+$(CH$_3$)$_3$I$^-$, —(CH$_2$)$_3$N(CH$_3$)$_2$, —(CH$_2$)$_4$(CH)(CONH$_2$)(NH$_2$), —CH(CONH$_2$)(CH$_2$)$_4$NH$_2$, —CH(CONH-adamantyl)(CH$_2$)$_4$NH$_2$, —CH(CH$_3$)(CH$_2$)$_3$N(C$_2$H$_5$)$_2$, —CH(CH$_3$)(CH$_2$)$_3$N$^+$(C$_2$H$_5$)$_2$(CH$_3$)I$^-$.

11. The threading intercalator according to claim 1, wherein R$^1$ and R$^2$ are both —(CH$_2$)$_3$-imidazole.

12. The threading intercalator according to claim 1, which has a structure of formula VII:

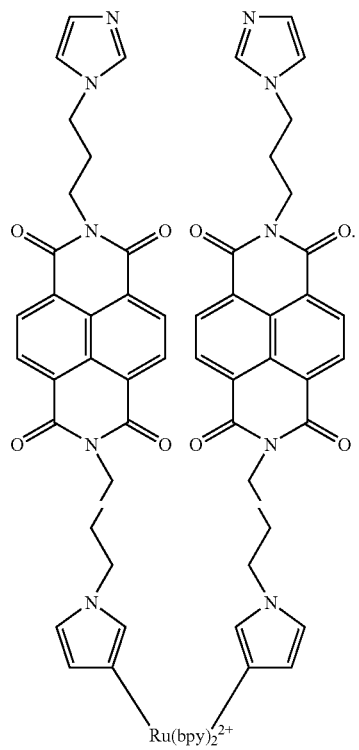

(VII)

13. The threading intercalator according to claim 1, which has a structure of formula VIII:

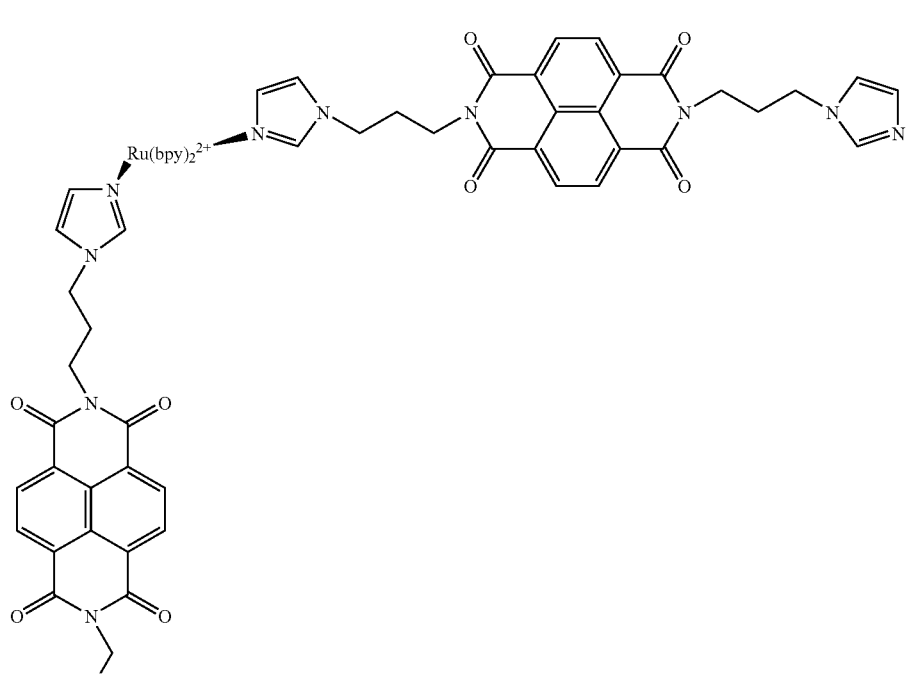

(VIII)

-continued

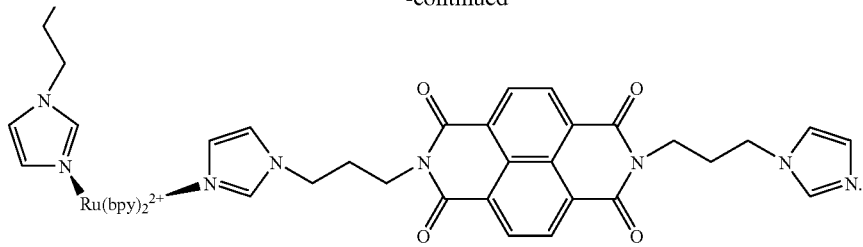

14. A complex comprising a double stranded nucleic acid molecule and a threading intercalator as claimed in claim 1, wherein the threading intercalator is intercarated in said double stranded nucleic acid molecule.

15. A process for detecting a single stranded nucleic acid molecule complementary to a nucleic acid probe immobilized onto an electrode substrate, which comprises the steps of:
   (a) contacting the probe molecules with an oligo- or poly-nucleotide sample in the presence of a threading intercalator as claimed in claim 1 to form by hybridization a complex comprising a double stranded hybrid of the probe molecules and the complementary single stranded nucleic acid molecules in the oligo- or poly-nucleotide sample, in which hybrid is intercalated the threading intercalator;
   (b) exciting the complex formed in step (a) by irradiating the complex with a light source or applying an electric current to the electrode; and
   (c) detecting photoluminescence or a change in voltametric peak current caused by a detectable group comprised in the threading intercalator.

16. A process for detecting a single stranded nucleic acid molecule complementary to a nucleic acid probe immobilized onto an electrode substrate, which comprises the steps of:
   (a) contacting the probe molecules with an oligo- or poly-nucleotide sample to form by hybridization a complex comprising a double stranded hybrid of the probe molecules and the complementary single stranded nucleic acid molecules in the oligo- or poly-nucleotide sample;
   (b) contacting a threading intercalator as claimed in claim 1 with the complex formed in step (a) so as to intercalate the threading intercalator into the complex formed in step (a);
   (c) exciting the complex formed in step (b) by irradiating the complex with a light source or applying an electric current to the electrode; and
   (d) detecting photoluminescence or a change in voltametric peak current caused by a detectable group comprised in the threading intercalator.

17. A kit for detecting a single stranded nucleic acid molecule complementary to a nucleic acid probe, which comprises an electrode substrate on which is immobilized the nucleic acid probe, and a threading intercalator as claimed in claim 1.

* * * * *